United States Patent [19]

Oroskar et al.

[11] Patent Number: 5,008,189

[45] Date of Patent: Apr. 16, 1991

[54] ENHANCED MEMBRANE SEPARATION OF MONOSACCHARIDES UTILIZING CONCENTRATION POLARIZATION

[75] Inventors: Anil R. Oroskar, Downers Grove; James L. Johnson, Des Plaines, both of Ill.

[73] Assignee: UOP, Des Plaines, Ill.

[21] Appl. No.: 369,433

[22] Filed: Jun. 20, 1989

Related U.S. Application Data

[63] Continuation-in-part of Ser. No. 895,115, Aug. 11, 1986.

[51] Int. Cl.$^5$ .................... C12P 19/02; C12P 19/20; B01D 61/00; B01D 61/14
[52] U.S. Cl. ..................................... 435/105; 127/55; 210/651; 210/654; 435/96; 435/205; 435/262; 435/280; 435/803
[58] Field of Search ................ 435/96, 105, 205, 262, 435/280, 803; 210/651, 654; 127/55

[56] References Cited

U.S. PATENT DOCUMENTS

| | | | |
|---|---|---|---|
| 3,720,583 | 3/1973 | Fisher | 435/205 |
| 3,769,175 | 10/1973 | Berdelle-Hilge | 435/819 |
| 4,132,595 | 1/1979 | Hebeda et al. | 435/96 |
| 4,414,401 | 11/1983 | Wintermeyer et al. | 549/370 |
| 4,511,654 | 4/1985 | Rohrbach et al. | 435/95 |
| 4,594,322 | 6/1986 | Thompson et al. | 435/95 |
| 4,751,003 | 6/1988 | Raehst et al. | 210/651 |
| 4,840,807 | 6/1989 | Yoshida et al. | 435/99 |

OTHER PUBLICATIONS

Cross et al., "Barrier Separation Processes" in Karger, B. L. et al., "An Introduction to Separation Science" (N.Y., John Wiley & Sons, Inc. 1973), pp. 469-478.

*Primary Examiner*—Herbert J. Lilling
*Attorney, Agent, or Firm*—Thomas K. McBride; Eugene I. Snyder

[57] ABSTRACT

Membrane separation of monosaccharides from an aqueous solution containing higher saccharides and saccharifying enzyme is considerably improved when the separation is performed under conditions where the polarization modulus for the enzyme is between 10 and 1,000, especially when the latter is between 50 and 500. A process utilizing this constraint affords a considerable savings in enzyme residence time and enzyme usage, and permits glucose of at least 94% purity to be prepared using membranes with a molecular weight cutoff as high as 70,000 with partial saccharification of thinned starch to give glucose levels in the range of 65-90%.

13 Claims, 1 Drawing Sheet

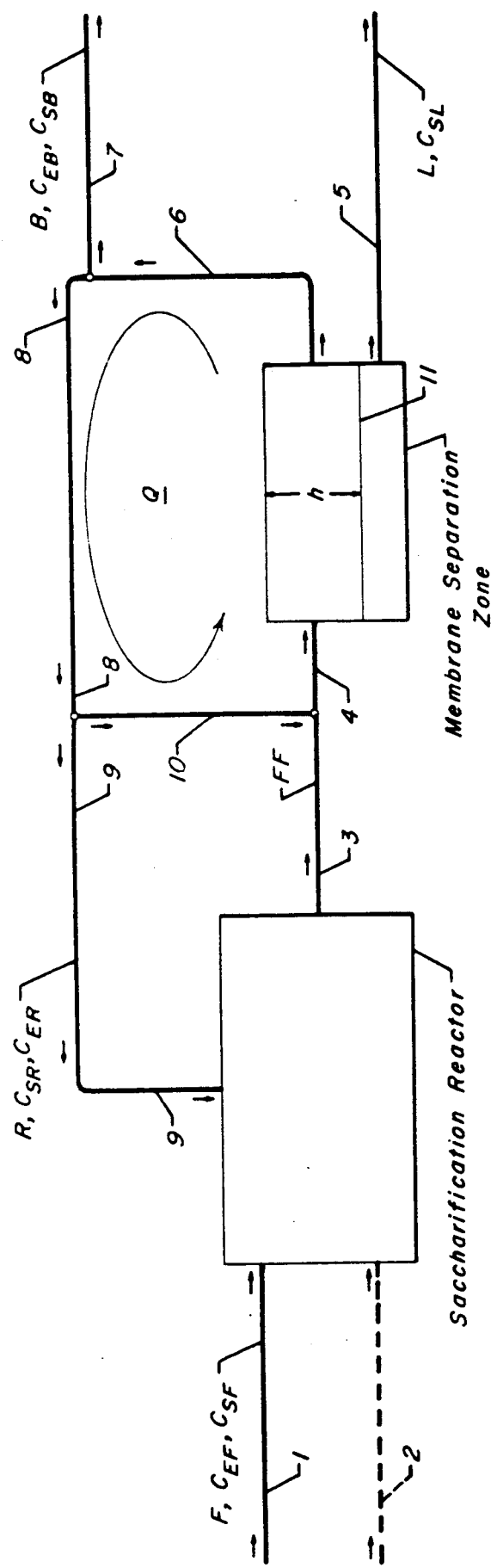

ENHANCED MEMBRANE SEPARATION OF MONOSACCHARIDES UTILIZING CONCENTRATION POLARIZATION

CROSS REFERENCE TO RELATED APPLICATION

This application is a continuation-in-part of our co-pending application, Ser. No. 895,115, filed Aug. 11, 1986, all of which is hereby incorporated by reference.

BACKGROUND OF THE INVENTION

Monosaccharides are staples in commerce with a diversity of uses, for example, the aldohexose glucose is used as a sweetener, as are the ketohexoses fructose and sorbose. Other monosaccharides, such as the pentoses arabinose and xylose, as well as glucose, often are used as the major component of fermentation media. Still other monosaccharides, such as mannose, are reduced to polyols such as mannitol and sorbitol, used as humectants and excipients in tablets.

The monosaccharides themselves generally are obtained by hydrolysis of polysaccharides, i.e., polymers having monosaccharides as their repeating units. Hydrolysis of polysaccharides sometimes is chemical, sometimes is enzymatic, and sometimes is a combination of both. For example, hydrolysis of starch, or saccharification as the process more often is called, may be a combination of acid and enzymatic (alpha-amylase) hydrolysis to afford partially hydrolyzed reaction mixture containing some mono-, di-, and trisaccharides, but composed mainly of polysaccharides with 4 or more monomeric units. Polysaccharides composed of n monomeric units often are referred to as having a "degree of polymerization n" or with the notation DPn; in this context partially hydrolyzed starch is mainly DP4, DP5, etc., collectively here designated as DP4+. The partially hydrolyzed starch, or a thinned starch as it is often called, is then further hydrolyzed enzymatically by amyloglucosidase (AG, or glucoamylase) to afford a mixture rich in monosaccharides (DP1), but also containing disaccharides (DP2), trisaccharides (DP3), and higher polysaccharides (DP4+).

To obtain pure monosaccharides, or nearly so, it is necessary to separate them from the di-, tri-, and higher polysaccharides in an aqueous solution which often contains the hydrolytic enzymes. Among the methods of separation which have been utilized is included membrane separation, that is, ultrafiltration using a membrane with a molecular weight cutoff low enough to reject materials of molecular weights substantially higher than the monosaccharide, but high enough to let the monosaccharide pass through at a high flux. The delicate balance between selectivity in rejecting unwanted components and a high flux through the membrane of a permeate rich in monosaccharides has spurred continued development of membranes having the requisite characteristics. During the course of the program to evaluate such membranes we encountered the phenomenon of concentration polarization whereby membrane rejected material, such as DP4+, tends to have locally extraordinarily high concentration at or near the membrane surface. Stated differently, there is often a steep, exponential gradient in the concentration of rejected species from the bulk of the feedstock toward the membrane surface, so that the concentration of such species at the membrane is many-fold greater than their concentration in the solution used as the feed. Generally such concentration polarization is undesirable since it may cause precipitation of the species congregating at the membrane surface leading to pore plugging, reduced flux, and a varying rejection coefficient. In fact, such was our observation when the feedstock was a synthetic mixture of DP1, DP2, DP3, and DP4+ prepared to match the characteristics of various partially hydrolyzed starch solutions. Concentration polarization can be minimized, for example, by transforming the feed flow from laminar to turbulent flow, or by reducing the height of the channel through which feedstock flowed. The reduction of concentration polarization was our initial task, and in fact reduction led to improved separation of monosaccharides through the membranes.

To our astonishment, when a feedstock of partially hydrolyzed starch containing the enzyme amyloglucosidase was passed over an ultrafiltration membrane under conditions where concentration polarization could be expected it was found that the separation of monosaccharides was substantially improved relative to the case where enzyme was absent. This unprecedented observation was examined in great detail, leading to our discovery that within a given, well defined range of AG enrichment at or near the membrane surface arising from concentration polarization, the separation of monosaccharides from the aforementioned mixture is enormously enhanced with little loss in flux. This stunning discovery has led to an improvement in the method of separating monosaccharides by ultrafiltration. Our discovery has further led to an improvement in the process of making glucose by partial saccharification of starch, separating the effluent stream into one enriched in monosaccharide and a stream depleted in monosaccharide but enriched in higher saccharides, and recycling the latter to the saccharification reactor. Such an underlying process recently has been described in U.S. Pat. No. 4,594,322 (compare U.S. Pat. No. 4,511,654) and will be further elaborated upon within.

SUMMARY OF THE INVENTION

In one aspect the invention herein is an improvement in the separation of monosaccharides from an aqueous solution containing monosaccharides, disaccharides, trisaccharides, higher polysaccharides, and the hydrolytic enzyme producing the monosaccharide by passing the solution over a membrane under conditions where the concentration of the enzyme at or near the membrane surface is some 10 to 1000 times that of the enzyme in the solution. An embodiment comprises passing the aqueous solution over a membrane where the stream flow is characterized by a Reynolds number of from 20 to 200. In a more specific embodiment, the monosaccharide is glucose and the enzyme is amyloglucosidase. In a still more specific embodiment, the solution contains from about 50 to about 94 percent glucose. In another embodiment the solution velocity is constrained to be within the range of 0.1 to 2 feet per second. In yet another aspect the invention is an improvement in the method of making glucose by partially hydrolyzing starch, separating the hydrolysate containing enzyme into a glucose-enriched stream by passing the hydrolysate under conditions approximating laminar flow over a membrane where the concentration of the enzyme near the membrane surface is from 10 to 1000 times that in the bulk solution, collecting the glucose-enriched permeate stream, and recycling the retentate stream partly to the saccharification zone and partly to the hydrolysate stream, while maintaining a bleed of retentate.

DESCRIPTION OF THE INVENTION

The object of our work leading to this invention was the separation of monosaccharides from an aqueous solution containing monosaccharides, disaccharides, trisaccharides, and higher polysaccharides, and also containing a hydrolytic enzyme responsible, at least in part, for forming such a mixture by the hydrolysis of higher molecular weight polysaccharides. We are particularly concerned with the separation of glucose from a mixture also containing DP2, DP3, and DP4+ as formed in the amyloglucosidase catalyzed hydrolysis of thinned starch. Such mixtures generally contain from about 50 to about 94 percent monosaccharide (glucose) with varying amounts of disaccharides, trisaccharides, and higher polysaccharides. For example, a partially hydrolyzed starch mixture containing about 75 percent glucose usually contains 3-6 percent DP2, similar amounts of DP3, and 13-19 percent DP4+; mixtures containing about 90 percent glucose typically contain from 2-4 percent DP2/DP3, and 6-8 percent DP4+.

Our initial work was directed toward testing the large number of membranes in the separation of glucose from a synthetic mixture which did not contain enzyme. During the screening of various ultrafiltration membranes, the effects of concentration polarization became apparent. As ultrafiltration proceeds, the rejected species tend to accumulate at the solution membrane interface. These species are transported away by diffusion, so that at steady state a concentration gradient exists at the interface in which the transport of these species toward the membrane by the bulk solution flow is balanced by the combined effect of diffusion flow in the opposite direction and flow through the membrane. This phenomenon of concentration polarization serves not only to decrease flux but also the filtrate purity. In some cases, the effect is so severe that a component may actually be precipitated on the membrane's surface effectively reducing its surface area or adding a second membrane in parallel.

The effect of concentration polarization cannot be entirely eliminated but may be reduced by operating with very narrow feed channels to reduce the concentration gradient that develops at a given fractional recovery of solute. The polarization modulus is an indication of the degree of concentration polarization occurring in a system and may be defined for a particular solute as the ratio of the concentration of the solute at the membrane surface to that in the bulk of the solution. Where there is complete rejection of a solute by the membrane, the polarization modulus under laminar flow conditions is given by, $$\frac{C_g}{C_b} = \exp\left(\frac{Jh}{D}\right)$$

where J is the flux through the membrane, h is the channel height, and D is the diffusivity of the rejected solute, $C_g$ and $C_b$ are the concentrations of the solute at the membrane and in the bulk, respectively, with the polarization modulus being the ratio $C_g/C_b$.

When the height of the flow channel was lowered, substantial improvements in both flux and glucose purities were obtained, which demonstrates the usual and expected results of increased separation efficiency with decreased concentration polarization.

EXAMPLE 1

The membrane holder consisted of 2 flanges between which the membrane was held. The feedstock entered the lower flange and flowed across the membrane surface through a flow channel cut into the flange surface. The filtrate or permeate, i.e., material which passes through the membrane, flowed out through the upper flange via a metallic porous plate inserted into a recess in the flange. The surface area of the membrane exposed to flow was 3 in$^2$ while the cross-sectional area of the flow channel was 0.105 in$^2$, and the length of the flow channel was 3 inches. The channel height could be reduced in a controlled manner by installation of 1 or more stainless steel inserts of a given thickness into the flow channel.

Rejection coefficients, $r^i$, are defined as, $$r^i = 100\left[1 - \frac{C_p^i}{C_f^i}\right]$$

where $C_p^i$ is the weight percent of component i in the permeate or filtrate, $C_f^i$ is its weight percent in the feed to the membrane, and $$C^i = DS \cdot m^i$$

where DS is the percent dry solids in the solution and $m^i$ is the percentage of component i relative to all saccharides in solution. Thus, if none of a component comes through the membrane $C_p = 0$ and the rejection coefficient is 100. If all of a component comes through a membrane $C_p = C_f$ and the rejection coefficient is 0. The performance of a membrane may be measured, in part, by its rejection coefficients for DP2, DP3, and DP4+ (ideally 100) especially relative to glucose (ideally 0). The Tables below show the effect of reducing channel height on the separation of glucose from a synthetic feedstock. Membrane A was a polyelectrolyte membrane with a molecular weight cutoff (MWCO) of 500, and B a cellulose acetate membrane with a MWCO of 1000.

TABLE 1

| Effect of Channel Height on Glucose Separation | | | | |
|---|---|---|---|---|
| Membrane | A | A | B | B |
| Channel height, in (cm) | .105(.267) | .015(.038) | .105(.267) | .015(.038) |
| Pressure, psi (kpa) | 500(3448) | 500(3448) | 300(2069) | 300(2069) |
| T, °C. | 70 | 60 | 60 | 60 |
| Feed rate, cc/min. | 580 | 500 | 580 | 500 |
| Filtrate flux$^a$ | 7.5 | 29.1 | 13.3 | 24.1 |
| Feed conc., % DS$^b$ | 33.2 | 28.1 | 31.0 | 39.8 |
| Filtrate conc., % DS$^b$ | 30.1 | 15.3 | 26.2 | 23.5 |
| Feed composition | | | | |
| % DP4+ | 16.3 | 15.3 | 15.4 | 14.7 |
| % DP3 | 3.6 | 4.0 | 3.5 | 3.9 |
| % DP2 | 4.6 | 5.3 | 5.5 | 5.8 |
| % DP1 | 75.5 | 75.4 | 75.6 | 75.6 |
| Filtrate composition | | | | |
| % DP4+ | 3.3 | 0.2 | 4.3 | 1.4 |
| % DP3 | 1.4 | 0.1 | 3.0 | 3.3 |
| % DP2 | 2.4 | 1.4 | 5.4 | 5.4 |
| % DP1 | 92.9 | 98.3 | 87.3 | 89.9 |
| Rejection coefficients | | | | |
| DP4+ | 82 | 99 | 76 | 92.5 |
| DP3 | 65 | 99 | 28 | 31.5 |
| DP2 | 53 | 86 | 17 | 26.6 |

TABLE 1-continued

| Effect of Channel Height on Glucose Separation | | | | |
|---|---|---|---|---|
| Membrane | A | A | B | B |
| DP1 | 0 | 29 | 3 | 6.2 |

[a] Flux is in units of gallons per square food of membrane per day.
[b] DS = dry solids.

As the preceding table shows in great detail, reducing the channel height results in a significant increase in filtrate (permeate) DP1 content. The increased rejection coefficients for DP2–DP4+ also demonstrate the beneficial effect of reduced concentration polarization in separating DP1 from the mixture.

The following table shows similar data for the DP1 content of the filtrate in lesser detail where the operating pressure, temperature, and feedstock is kept constant.

TABLE 2

| Further Effects of Channel Height on Glucose Separation | | | | |
|---|---|---|---|---|
| Membrane | A | A | B | B |
| Channel height, inches (cm) | flux[a] | purity[b] | flux[a] | purity[b] |
| 0.105(.267) | 7.5 | 92.9 | 16.0 | 86.1 |
| 0.022(.056) | 13.0 | 98.7 | 22.2 | 89.6 |
| 0.015(.038) | 29.1 | 98.3 | 28.2 | 91.1 |
| 0.013(.033) | 28.9 | 98.2 | 32.4 | 90.2 |

[a] Flux is in units of galons per square foot of membrane per day.
[b] Weight percent of total solids.

The effect of varying channel height and flux on the polarization modulus was calculated from the equation reproduced above and is summarized in Table 3 below, where the diffusivity of DP4+ was taken to be $1.0 \times 10^{-5}$ cm$^2$/sec.

TABLE 3

| Polarization Modulus for DP4+ In Glucose Ultrafiltration for Laminar Flow Operation | | | |
|---|---|---|---|
| Channel Height, | J = 1 GFD | J = 10 GFD | J = GFD |
| 0.105(0.267) | 3.5 | $2.8 \times 10^5$ | $2.3 \times 10^{16}$ |
| 0.05(0.127) | 1.8 | 396 | $6.2 \times 10^7$ |
| 0.01(0.0254) | 1.1 | 3.3 | 36 |

The encouraging results from the synthetic feedstocks accompanying reduction of the effects of concentration polarization were followed by the use of feedstocks from starch hydrolysis still containing active AG. To our astonishment, ultrafiltration produced a higher purity filtrate than was produced in the absence of enzyme.

EXAMPLE 2

Membrane separations of feedstocks resulting from the partial hydrolysis of starch and still containing active enzymes were performed as described in the prior example. Some results, tabulated below, unequivocally show the improvement in membrane separation when enzyme is present in the feed. Membrane C a is cellulose acetate membrane with a molecular weight cutoff of 1,000; membrane D is a polysulfone membrane with the same cutoff.

TABLE 4

| Comparison of Membrane Separation With and Without Enzyme | | | | |
|---|---|---|---|---|
| Membrane | C | C | D | D |
| Enzyme | Yes | No | Yes | No |
| Channel height, in (cm) | .026(.066) | .015(.038) | .015(.038) | .015(.038) |
| Pressure, psig (kpa) | 150(1034) | 300(2069) | 150(1034) | 300(2069) |
| Flux, GFD | 13.3 | 49.1 | 11.1 | 42.6 |
| Feed | | | | |
| solids | 34.9 | 26.9 | 33.5 | 27.1 |
| DP4+ | 17.1 | 14.8 | 14.3 | 15 |
| DP1 | 80 | 76.2 | 83.1 | 75.0 |
| Filtrate | | | | |
| solids | 29.9 | 23.9 | 29.3 | 24.3 |
| DP4+ | 3.2 | 6.9 | 5.0 | 8.8 |
| DP1 | 93.0 | 83.9 | 90.5 | 82 |
| Rejection coefficients | | | | |
| DP4+ | 84 | 58.3 | 69.4 | 45.2 |
| DP1 | 0.4 | 2.2 | 4.8 | 3.3 |

The data above and those from similar experiments showed that incorporation of enzyme into the membrane system leads to a synergism between the membrane surface and the enzyme boundary layer or gel layer, which develops due to concentration polarization. In effect, this concentrated enzyme layer behaves as a small bioreactor, serving to further convert those higher molecular weight species diffusing through to the membrane surface. However, this enzyme gel layer also acts as an additional barrier to diffusion, inducing a flux penalty while improving the filtrate purity. Proper control of this gel layer is crucial to the success of any process dependent upon it and is discussed in further detail below.

It has been found that when the polarization modulus for the enzyme is about 10, there are some benefits accruing from the enzyme gel layer, but the benefits are marginal. With a polarization modulus between about 50 and about 500 definite positive effects of the gel layer are observed. When the polarization modulus is greater than about 1,000, and particularly greater than about 10,000, glucose begins to revert to isomaltose, which is a bitter principal to be avoided in the preparation and purification of glucose. Consequently, in the practice of our invention it is necessary to have the polarization modulus of the enzyme between about 10 and about 1,000, and preferably between about 50 and about 500. Maintenance of the polarization modulus under laminar flow conditions within the aforementioned ranges is at the nub of our invention.

The operational parameters necessary for proper maintenance of the polarization modulus within the aforementioned range are similarly constrained to lie within a well-defined range. In particular, the feedstock stream flow in the practice of our invention is characterized by a Reynolds number in the range from about 20 to about 200.

The Reynolds number, R, is given by the equation $$R = \frac{h \times v \times d}{\eta}$$

where
  h = channel height
  v = linear velocity of stream
  d = density of stream
  $\eta$ = viscosity of stream Both stream density and viscosity can be varied only within quite narrow ranges, so that h and v are the only independent variables for practical purposes. Stream velocity is constrained to be within limits as low as about 0.1 ft/sec and up to about 2 ft/sec, but the range 0.5–1.0 ft/sec is most desirable. Channel height also is subject to the constraint of being at least 0.02 cm but no more than 0.2 cm.

When the enzyme gel layer is maintained at a polarization modulus between about 10 and about 1,000, and especially between about 50 and about 500, it is found that (1) the purity of the product monosaccharide is relatively independent upon the kind of membrane used, and (2) the glucose concentration is close to $G_{max}$, the maximum purity attained in a soluble AG saccharification reaction. Within the gel layer the enzyme concentration reaches about 100 units per gram of dry solids. At such an extraordinarily high local enzyme concentration, the reaction to produce glucose is taken to completion with any reasonable composition of the membrane feedstock. If a membrane is of sufficiently large molecular weight cutoff, it will pass virtually the entire product mixture but for enzyme freely, whereas membranes with a smaller molecular weight cutoff will further increase glucose product purity. In particular, where glucose purity up to about 93–94 percent is acceptable, membranes with a molecular weight cutoff as high as 70,000 may be employed in our invention. Where glucose purities above this level are desired membranes with a lower molecular weight cutoff need to be employed. In particular, ultrafiltration membranes with a molecular weight cutoff of about 10,000 are sufficient to afford glucose purity on the order of 96–7 percent, and membranes with a molecular weight cutoff of about 500 afford glucose purity of about 99 percent, it being understood that in all cases separation is effected within the limits of the polarization modulus stated above.

EXAMPLE 3

In the following examples performance data on the separation of glucose by ultrafiltration are given for various membranes in the presence and absence of enzyme. Membranes E and D were polysulfones from different suppliers, and C was a cellulose acetate.

TABLE 5

| Membrane | C | C | E | E | D | D |
|---|---|---|---|---|---|---|
| MWCO | 1,000 | 1,000 | 10,000 | 10,000 | 1,000 | 1,000 |
| Enzyme present | no | yes | no | yes | no | yes |
| Rejection coefficients | | | | | | |
| DP4+ | 69.2 | 92.4 | 69.9 | 78.5 | 55.0 | 75.8 |
| DP3 | 22.8 | 44.4 | 21.5 | 33.0 | 26.7 | 36.7 |
| DP2 | 16.2 | 11.2 | 21.4 | 33.2 | 19.7 | 24.0 |
| DP1 | 5.7 | 5.5 | 7.0 | −1.9 | 7.5 | −0.1 |

Effect of Enzyme on Rejection Coefficients

As the data clearly show, the rejection coefficients for DP3 and DP4+ are substantially greater in the presence of enzyme, whereas that for DP1 is unchanged or decreased. What this means is that the membranes are more selective in passing glucose at the expense of tri- and higher oligosaccharides when enzyme is present.

The phenomenon of concentration polarization is a universal one which can be utilized generally to enhance product formation in virtually any enzyme-mediated process. The process flowchart in FIG. 1 depicts the basic process as applied to glucose arising from saccharification of thinned starch. As discussed below many variants are possible, and it needs to be appreciated that however important may be the process of saccharification the particular process of FIG. 1 is merely illustrative of a more general theme.

Briefly, a feedstock, in this case thinned starch, enters a saccharification zone at 1. Although the feedstock normally will contain the enzyme amyloglucosidase, the enzyme can be separately added as indicated by the dashed line 2. Effluent from the saccharification reactor, FF, is the reaction product stream and is sent to the membrane separation zone. The permeate or filtrate is removed at 5, and the retentate is recycled at 6. Part of the retentate is removed at 7 through a bleed, B, part is recycled to the saccharification zone at 9, and the remainder of the retentate is mixed with the reactor effluent and returned to the membrane separation zone via 4. Multiple saccharification zones are possible as one modification of this basic flow scheme. Another modification may be multiple separation zones, either in parallel or in series. Yet other modifications may have the bleed stream being sent to other separation zones where there is more than one present.

Turning to the specific case where the flow scheme is applied to the production of glucose, F is the feedstock of thinned starch. For the purpose of this application, thinned starch is partially degraded starch containing a minor proportion of monosaccharides, up to about 10 percent but generally less than about 4 percent, and a distribution of polysaccharides, where from about 20 percent to about 70 percent are present as disaccharides (DP2) through heptasaccharides (DP7), with from about 30 percent to about 80 percent present as DP8 and higher molecular weight polysaccharides. The feedstock contains starch at a concentration generally given on a weight percent dry solids basis as designated by $C_{SF}$, and also contains the starch-degrading enzyme amyloglucosidase at a concentration of $C_{EF}$. However, it is possible to add the soluble AG through a separate line 2. The mixture of thinned starch and soluble AG is then maintained in the saccharification zone, usually a stirred tank reactor, for a time sufficient to achieve the desired level of glucose formation. For all practical purposes saccharification is continued to a glucose level from about 65% to about 90% (on a dry solids basis), and even more typically to a level between about 70 and 90%. The reactor effluent, FF, is continuously drawn off at 3 and sent to a membrane separation unit. The separation feed is passed over the membrane, 11, through a narrow channel whose height is designated by h. Permeate, L, is removed at 5 and has a dry solids content designated by $C_{FL}$. The retentate, or that portion of the feed to the membrane separator which does not pass through the membrane, is withdrawn at 6 to form the upper loop as shown in the Figure. Part of this retentate is directed toward a bleedstream, B, which contains enzyme at a concentration $C_{EB}$ and a mixture of saccharides at a concentration $C_{SB}$. Another part of the retentate is recycled to the saccharification zone at 9. This recycled stream, R, also contains enzyme at a concentration of $C_{ER}$ and polysaccharides at a concentration $C_{SR}$. The remainder of the retentate is recycled via 10 and mixed with the reactor effluent to re-enter the membrane separation zone as shown at 4.

The process is completely defined by its independent variables. The residence time of the enzyme, $t_r$, may be defined by V/F, where V is the volume of the entire system. However, since the volume of the remainder of the system generally is quite small relative to the reaction volume in the saccharification zone, V may be effectively equated with the latter. The enzyme half-life, $t_{\frac{1}{2}}$, is determined by the source of the enzyme and the temperature at which saccharification is conducted. It is generally desirable to minimize the ratio $t_r/t_{\frac{1}{2}}$ in order to minimize denaturation of AG; minimum denaturation is desirable to maximize enzyme activity in the gel layer at the membrane surface. The quantities F/L, B/L, and FF/L are conveniently controlled independent variables, especially taken with the mass balance equations, $$F=B+L, \text{ and}$$

$$FF=B+R+L$$

Within the recycle loop, the sweep velocity is designated by Q. Denatured protein tends to aggregate on the surface of the gel layer, to the detriment of the separation process, and it has been found desirable to have a high sweep velocity to sweep off the accumulated denatured protein. Having a small bleed, B, in the system also aids in preventing the accumulation of denatured protein. The membrane separation zone works under conditions of concentration polarization where the polarization modulus is within the range described above, viz., between about 10 and about 1,000, and preferably between about 50 and about 500. It is therefore necessary to have a channel height, h, of such a magnitude as to maintain the proper polarization modulus. Other independent variables include the concentration of saccharides and enzyme in the feedstock, $C_{FF}$ and $C_{EF}$, respectively. Membrane characteristics such as the flux through the membrane, J, and the rejection coefficients, r, for the various components of the feed entering the membrane separation zone are additional independent variables. Finally, the temperature at which both saccharification and separation are conducted as well as their pressures are additional independent variables. Note that the concentration of saccharides in the permeate, bleed, and retentate streams, as well as the concentration of enzyme in the bleed and retentate streams, are determined by the nature of the membrane and the value of the other independent parameters.

Within the context of the aforementioned description, the stream flow over the membrane is characterized by a Reynolds number from about 20 to about 200. The channel height may be as low as about 0.02 cm up to about 0.2 cm. The stream velocity needs to be at least about 0.1 feet per second, and may be as great as 2 feet per second. The preferred stream velocity is in the range of about 0.5 to about 1.0 feet per second.

The process for the production of glucose from the saccharification of thinned starch as practiced according to the description above, is best conducted between about 40 and about 65 degress C. Lower temperatures increase the half life of the enzyme but also decrease reaction rate. The pressure in the saccharification zone generally will be about atmospheric pressure. Higher pressures can be used, although there are no beneficial effects of increased pressure, at least through pressures of several atmospheres. In the membrane separation zone pressures are typically on the order from about 50 to about 500 psig, but this will be determined in part by the strength of the membrane and the flux through the membrane.

The residence time of the AG in the reactor is desirably between about 1 and about 24 hours, and even more typically between about 3 and about 10 hours. This needs to be compared with a conventional residence time of about 48–72 hours, which demonstrates the substantial reduction in reaction time effected by our process. The half life of AG is dependent upon reaction temperature but typically will be on the order of 100 hours. As stated previously, the ratio $t_r/t_{\frac{1}{2}}$ is desirably as low as possible, and those in the range between about 0.02 and 0.2, and more particularly between about 0.04 and 0.1, are preferred. The ratio F/L usually is between 1.01 and about 1.10. Remembering that F=B+L, this means that B/L is between 0.01 and about 0.1. In other words, from about 1 to about 10 percent of the incoming feed is removed in the bleed stream. The ratio FF/L is usually from about 1.5 to about 3.0. From the mass balance equation, FF=B+R+L, it can then be seen that the stream R recycled to the reactor is between about 0.4 and about 2.0 times as great as the permeate stream.

The sweep velocity, Q, is between about 0.1 and about 2 feet per second at a channel height of between about 0.01 to about 0.1 inches. The dry solids content of the feedstock, $C_{SF}$, is between about 20 and about 40 percent by weight, with conventional saccharification reactors operating at about 30 percent dry solids. The concentration of saccharifying enzyme, AG, is normally between about 0.05 to about 0.25 units per gram of dry solids, but more usually is in the range from about 0.04 to about 0.10 units per gram of dry solids. Present commercial practice uses about 0.23 units per gram of dry solids AG, which shows the enzyme savings attained in our process.

As to the membrane characteristics, the nature of the membrane is not particularly important so long as it is chemically unreactive to the product mixture and has sufficient mechanical strength to be used for a time long enough to be commercially feasible, so long as the membrane flux and rejection coefficients satisfy some minimum criteria. Commercial feasibility often requires that the membrane flux be at least 1 GFD, and a flux between about 1 and about 30 GFD will be generally suitable. Of course, an even higher flux would be beneficial, although realistically this has not been possible with membranes having suitable rejection coefficients for the enzyme and the various saccharide components. Rejection coefficients for DP4+ should be from about 50 to about 95 percent, those for DP3 between about 30 and about 70 percent, for DP2 between about 10 and about 30 percent, DP1 less than about 10 percent, and the rejection coefficient for the enzyme should be greater than 99 percent.

EXAMPLE 4

This example shows how changing the combination of residence time and enzyme dosage affects the enzyme/membrane synergism. Any given reactor effluent composition can be achieved by different combinations of residence time and enzyme dosage. Two combinations are shown, one with low residence time and high enzyme dosage, and another with a higher residence time and a lower enzyme dosage. The table shows that the case with higher enzyme dosage and lower residence time affords retentates and filtrates similar to those in the other case.

TABLE 6

| Effect of Residence Time and Enzyme Dosage | | |
| --- | --- | --- |
| Enzyme Dosage, $\mu/g$ | 0.053 | 0.090 |

TABLE 6-continued

| Effect of Residence Time and Enzyme Dosage | | |
|---|---|---|
| Residence Time, Hours | 6.7 | 3.3 |
| Reactor Effluent | | |
| % DS | 33.0 | 32.1 |
| % DP1 | 85.3 | 83.2 |
| % DP2 | 3.7 | 4.4 |
| % DP4+ | 10.4 | 11.8 |
| Retentate | | |
| % DS | 33.9 | 33.8 |
| % DP1 | 87.0 | 86.3 |
| % DP2 | 3.2 | 3.3 |
| % DP4+ | 9.2 | 9.7 |
| Filtrate 1[a] | | |
| % DS | 31.1 | 30.2 |
| % DP1 | 94.0 | 93.9 |
| % DP2 | 3.3 | 3.3 |
| % DP4+ | 2.0 | 2.3 |
| Filtrate 2[b] | | |
| % DS | 30.7 | 29.6 |
| % DP1 | 95.2 | 95.3 |
| % DP2 | 3.2 | 3.0 |
| % DP4+ | 1.1 | 1.3 |

[a]Membrane used is a cellulose acetate with MWCO of about 1,000.
[b]Membrane used is polyelectrolyte with a MWCO of 500–1000.

EXAMPLE 5

This example uses a kinetic model based on extensive experimental data to show the benefits of enzyme/membrane synergism. The first case is one in which the membrane performance is not affected by the gel layer; separation occurs solely by membrane rejection. The second case holds all operating parameters constant but includes the effect of enzyme synergism, i.e., it includes the effects of concentration polarization of AG. The third case also uses concentration polarization with the enzyme dosage being decreased until a product similar to that of the first case was achieved. Operating conditions were representative of pilot plant data. In all cases the feed had 30% dry solids.

TABLE 7

| Effect of Concentration Polarization of Enzyme in Glucose Production | | | |
|---|---|---|---|
| Case No. | 1 | 2 | 3 |
| FF/L | 2.11 | 2.11 | 2.11 |
| Enzyme Dosage, μ/g | 0.056 | 0.056 | 0.016 |
| Residence Time, Hrs | 4.7 | 4.7 | 4.7 |
| Reactor Effluent | | | |
| % DS | 31.9 | 34.3 | 37.4 |
| % DP1 | 84.7 | 84.9 | 65.6 |
| % DP2 | 5.3 | 5.5 | 7.1 |
| % DP4+ | 9.5 | 9.1 | 25.8 |
| Retentate | | | |
| % DS | 32.3 | 36.0 | 0.7 |
| % DP1 | 83.2 | 88.3 | 66.1 |
| % DP2 | 5.2 | 4.9 | 6.5 |
| % DP4+ | 11.1 | 6.6 | 26.4 |
| Filtrate | | | |
| % DS | 31.0 | 31.4 | 31.3 |
| % DP1 | 88.2 | 94.2 | 88.8 |
| % DP2 | 5.3 | 5.2 | 8.0 |
| % DP4+ | 6.0 | 0.4 | 2.0 |

These results clearly show that at the same enzyme dosage and residence time, the filtrate has 6% more glucose arising from the effects of the enzyme gel layer (Cases 1 and 2). To obtain similar filtrates at the same residence time, only 30% as much enzyme is needed because of the effects of the enzyme gel layer (Cases 2 and 3).

What is claimed is:

1. In the separation of monosaccharides from an aqueous stream containing a mixture of monosaccharides, disaccharides, trisaccharides, higher oligosaccharides, and a saccharifying enzyme by flowing the stream over a membrane through a channel and collecting the permeate enriched in monosaccharide, the improvement consisting of performing the separation under conditions where the flowing stream is characterized by a Reynolds number from about 20 to about 200 subject to the constraints that (1) the channel height is between about 0.02 and about 0.2 cm, and (2) the stream has a velocity between about 0.1 and about 2 feet per second.

2. The separation of claim 1 where the stream velocity is between 0.5 and 1.0 feet per second.

3. The separation of claim 1 where the enzyme is amyloglucosidase.

4. The separation of claim 1 where the membrane has a molecular weight cutoff up to about 70,000.

5. The separation of claim 4 where the membrane has a molecular weight cutoff up to about 10,000.

6. The separation of claim 5 where the membrane has a molecular weight cutoff up to about 500.

7. A method of making glucose comprising hydrolyzing in a saccharification zone a feedstock of thinned starch under the action of a soluble saccharifying enzyme to a reaction product stream containing from about 65 to about 90 percent glucose, flowing said product stream to a membrane separation unit operating under conditions where the flowing stream has a Reynolds number between about 20 and about 200 and a stream velocity between about 0.1 and about 2.0 feet per second, and the channel height in the membrane separation unit is between about 0.02 and about 0.2 cm to afford a permeate stream containing at least about 94 percent glucose and a membrane retentate, collecting the permeate stream, removing from the retentate a bleed stream which is from about 0.01 to about 0.1 that of the permeate stream, recycling a portion of the retentate stream to the saccharification zone and mixing the remaining portion of the retentate stream with the product stream prior to passing the mixture to the membrane separation unit.

8. The method of claim 7 where the stream velocity is between 0.5 and 1.0 feet per second.

9. The method of claim 7 where the enzyme is amyloglucosidase.

10. The method of claim 7 where the membrane has a molecular weight cutoff up to about 70,000.

11. The method of claim 10 where the membrane has a molecular weight cutoff up to about 10,000.

12. The method of claim 11 where the membrane has a molecular weight cutoff up to about 500.

13. The method of claim 7 where the enzyme has a residence time in the system between about 0.02 and about 0.2 that of its half-life, the ratio of the feedstock to permeate streams is about 1.01 to about 1.10, the stream recycled to the saccharification zone is from about 0.4 to about 2.0 times as great as the permeate stream, and where the ratio of the total membrane feed stream to permeate stream is from about 1.5 to about 3.0.

* * * * *